US012357351B2

(12) United States Patent
Levine (10) Patent No.: US 12,357,351 B2
(45) Date of Patent: *Jul. 15, 2025

(54) RETRACTOR/COMPRESSION/DISTRACTION SYSTEM

(71) Applicant: Genesys Orthopedic Systems, L.L.C., Austin, TX (US)

(72) Inventor: Marc J. Levine, Richboro, PA (US)

(73) Assignee: Genesys Orthopedic Systems, L.L.C., Austin, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/611,909

(22) Filed: Mar. 21, 2024

(65) Prior Publication Data

US 2024/0299066 A1  Sep. 12, 2024

Related U.S. Application Data

(63) Continuation of application No. 17/506,957, filed on Oct. 21, 2021, now Pat. No. 11,937,856, which is a
(Continued)

(51) Int. Cl.
*A61B 17/70* (2006.01)
*A61B 17/02* (2006.01)
(Continued)

(52) U.S. Cl.
CPC ........ *A61B 17/708* (2013.01); *A61B 17/0206* (2013.01); *A61B 17/0218* (2013.01);
(Continued)

(58) Field of Classification Search
CPC ....................................... A61B 17/7074–7092
See application file for complete search history.

(56) References Cited

U.S. PATENT DOCUMENTS 4,957,495 A * 9/1990 Kluger ............... A61B 17/7077
606/264
5,219,349 A * 6/1993 Krag .................. A61B 17/7077
606/53
(Continued)

OTHER PUBLICATIONS

"InViZia® Anterior Cervical Plate System", Zimmer Biomet Spine Surgical Technique Guide, 2017, 28 pages.
(Continued)

*Primary Examiner* — Eduardo C Robert
*Assistant Examiner* — Steven J Cotroneo
(74) *Attorney, Agent, or Firm* — Trop, Pruner & Hu, P.C.

(57) ABSTRACT

A minimally invasive system for retraction, compression and distraction includes a tap having a shaft with threads and a head, a blade having a proximal end and a distal end and a base removably mountable to the proximal end. The tap is configured to form screw threads in a bone. The distal end is mountable to the head. The blade is pivotable relative to the head in a mounted configuration. The blade is configured to facilitate soft tissue retraction in the mounted configuration. The base is configured to manipulate the blade to retract and compress segments of the bone. The base is configured to provide distraction and/or compression using the provisional taps either directly or through the use of blades, insertion devices or tubes. The blades may be used to retract tissue and provide a visual field either independent or in conjunction with the provisional taps, insertion devices or tubes.

15 Claims, 5 Drawing Sheets

Related U.S. Application Data continuation of application No. 15/833,737, filed on Dec. 6, 2017, now Pat. No. 11,154,336.

(60) Provisional application No. 62/430,465, filed on Dec. 6, 2016.

(51) Int. Cl.
*A61B 17/16* (2006.01)
*A61B 17/68* (2006.01)

(52) U.S. Cl.
CPC ........ *A61B 17/025* (2013.01); *A61B 17/1655* (2013.01); *A61B 17/7079* (2013.01); *A61B 2017/0256* (2013.01); *A61B 2017/681* (2013.01); *A61B 17/7032* (2013.01)

(56) References Cited

U.S. PATENT DOCUMENTS

| | | | | |
|---|---|---|---|---|
| 5,728,046 | A * | 3/1998 | Mayer | A61B 17/0293 |
| | | | | 600/210 |
| 7,494,463 | B2 * | 2/2009 | Nehls | A61B 17/0206 |
| | | | | 606/105 |
| 7,664,544 | B2 * | 2/2010 | Miles | A61B 5/1106 |
| | | | | 600/554 |
| 7,927,337 | B2 * | 4/2011 | Keller | A61B 17/025 |
| | | | | 606/90 |
| 8,357,184 | B2 * | 1/2013 | Woolley | A61B 17/0206 |
| | | | | 606/279 |
| 8,636,655 | B1 * | 1/2014 | Childs | A61B 17/0206 |
| | | | | 600/219 |
| 9,414,828 | B2 * | 8/2016 | Abidin | A61B 17/025 |
| 9,795,370 | B2 * | 10/2017 | O'Connell | A61B 17/02 |
| 11,154,336 | B2 | 10/2021 | Levine | |
| 11,937,856 | B2 * | 3/2024 | Levine | A61B 17/1655 |
| 2002/0035360 | A1 | 3/2002 | Connors et al. | |
| 2003/0073998 | A1 * | 4/2003 | Pagliuca | A61B 17/0293 |
| | | | | 606/264 |
| 2003/0149341 | A1 * | 8/2003 | Clifton | A61B 17/0206 |
| | | | | 600/210 |
| 2003/0233138 | A1 | 12/2003 | Spooner | |
| 2004/0015157 | A1 | 1/2004 | Connors et al. | |
| 2004/0147985 | A1 | 7/2004 | MacFarland et al. | |
| 2006/0122585 | A1 | 6/2006 | Connors et al. | |
| 2007/0093828 | A1 * | 4/2007 | Abdou | A61B 17/7077 |
| | | | | 606/86 A |
| 2008/0077138 | A1 * | 3/2008 | Cohen | A61B 17/708 |
| | | | | 606/86 A |
| 2009/0227845 | A1 * | 9/2009 | Lo | A61B 17/0206 |
| | | | | 600/210 |

OTHER PUBLICATIONS

"TiLock2 Spinal System", Genesys Spine® Surgical Technique, date unknown, 24 pages.
"Pilot Hole", Wiktionary, Jun. 2, 2017, 1 page, https://en.wiktionary.org/wiki/pilot_hole.
"Closed curve," Math.net, downloaded from https://www.math.net/closed-curve on Apr. 23, 2021.

* cited by examiner

FIG. 15

RETRACTOR/COMPRESSION/DISTRACTION SYSTEM

CROSS-REFERENCE TO RELATED APPLICATIONS

This application is a continuation of U.S. patent application Ser. No. 17/506,957 filed Oct. 21, 2021, which is a continuation of U.S. patent application Ser. No. 15/833,737, filed Dec. 6, 2017, now U.S. Pat. No. 11,154,336, issued Oct. 26, 2021, which claims priority to U.S. Provisional Patent Application No. 62/430,465, filed Dec. 6, 2016 and entitled "Retractor/Compression/Distraction System". The content of each of the above applications is hereby incorporated by reference.

BACKGROUND OF THE INVENTION

Retractor systems for minimally invasive ("MIS") surgery are designed to retract off of permanent screws placed in bone or with free standing systems ("FSS") that are independent of any implanted device which are attached to the bones. These retraction systems may be free standing or often require attachment to a stable structure, such as the surgical table via arm-like attachments. Similarly, compression/distraction of spine segments is typically accomplished via permanently placed screws/pins/nails/hooks that are left implanted in the patient.

There is no readily known retractor system design available that is universal for nearly any cannulated screw system that provides the technical advantage of applying retraction/compression/distraction by connecting to a temporary/provisionally inserted device attached to the bone, such as a tap. All current non-FSS systems typically require the placement of permanent screws in order to distract/compress/retract. This limitation of retractor availability and function has resulted in many companies being unable to compete in the market of minimally invasive spine surgery, because each screw system is typically tied to a specific retractor, distractor, compression instrument and technique. Systems may also utilize disposable pins to mount to bones for compression, but such systems require disposal of the relatively expensive pins following use, which is a generally inefficient use of the pins.

The preferred present invention addresses the deficiencies of the known prior art systems and methods, permitting use of nearly any cannulated pedicle screw with the system.

SUMMARY OF THE INVENTION

Briefly stated, the preferred invention is directed to a minimally invasive system for retraction, compression and distraction during a surgical procedure. The preferred system is not limited to MIS procedures and may be utilized with generally open or partially open procedures and for numerous surgical procedures, but, most preferably, for spinal procedures. Procedures that may benefit from the use of the preferred system include, but are not limited to, anterior, posterior and lateral cervical decompression and fusion procedures, general cervical procedures, thoracic procedures, lumbar procedures, sacrum and pelvis procedures, skull procedures and numerous additional procedures where distraction, compression and/or retraction is desirable. The system includes a tap having a shaft with threads and a head, a blade having a proximal end and a distal end and a base removably mountable to the proximal end. The tap is configured to form screw threads in a bone and for removal from the bone before the completion of the surgical procedure. The distal end is mountable to the head. The blade is pivotable relative to the head in a mounted configuration. The blade is configured to facilitate soft tissue retraction in the mounted configuration to create a surgical path to a surgical site. The base is configured to manipulate the blade to retract and compress segments of the bone during the surgical procedure. The blade may be configured to pivot or hinge from its proximal end to assist with retraction of soft tissue and create a wider field of vision at the surgical site. The blade may also be configured to pivot or hinge from alternative or multiple positions, such as near a middle portion of the blade or proximate a distal end of the blade. The blade is also preferably selectively lockable in numerous positions to maintain a preferred surgical path.

The preferred minimally invasive retractor uniquely allows retraction/compression/distraction via provisionally placed implants which are eventually removed and allows placement of already existing screw systems. Because of its design it allows for optimal visualization and working space to perform a desired surgical procedure. In another embodiment the preferred retractor system may be used without the eventual placement of permanent screws that replace the provisional tap. In another embodiment the preferred retractor system and the preferred taps can be used for parts of the procedure and substituted at appropriate times during the procedure for another existing system.

The preferred system is utilized for MIS or open decompressions/fusions/spine surgery that compress/distract/retract off of a provisional tap that is used to create threads in a hole drilled in a bone. This tap may be used to create a path for cannulated or solid screws such that the threads of the non-tapping screws follow the pre-formed threads in the bone from the tap. This system can be used for nearly any screw based system in the spine, such as for a cannulated pedicle screw or a solid screw that is driven into a pre-formed and threaded hole formed by taps.

The preferred system utilizes a non-screw or non-permanent implant, provisionally placed component, such as a pin, screw, tap, threaded component, solid component or other implement or instrument whose purpose is to be provisional and may be replaced by a final implant such as a screw.

The preferred retractor system allows competition among orthopedic and spinal implant companies by permitting use of nearly any screw with the preferred system, thereby bringing down the cost of spine surgery. The need to spend money and resources on additional research and development will be limited or avoided, as pre-existing screw systems will be able to be used either for the first time and/or more effectively with the preferred universal minimally invasive retractor/compression/distraction system.

BRIEF DESCRIPTION OF THE DRAWINGS

The foregoing summary, as well as the following detailed description of preferred embodiments of the instrument, implant and method of the present application, will be better understood when read in conjunction with the appended drawings. For the purposes of illustrating the universal minimally invasive retractor/compression/distraction system, there are shown in the drawings preferred embodiments. It should be understood, however, that the application is not limited to the precise arrangements and instrumentalities shown. In the drawings.

DETAILED DESCRIPTION OF THE INVENTION

Certain terminology is used in the following description for convenience only and is not limiting. Unless specifically set forth herein, the terms "a", "an" and "the" are not limited to one element but instead should be read as meaning "at least one". The words "right", "left", "lower" and "upper" designate directions in the drawings to which reference is made. The words "inwardly" or "distally" and "outwardly" or "proximally" refer to directions toward and away from, respectively, the patient's body, or the geometric center of the preferred universal minimally invasive retractor/compression/distraction system and related parts thereof. The words, "anterior", "posterior", "superior," "inferior", "lateral" and related words and/or phrases designate preferred positions, directions and/or orientations in the human body to which reference is made and are not meant to be limiting. The terminology includes the above-listed words, derivatives thereof and words of similar import.

It should also be understood that the terms "about," "approximately," "generally," "substantially" and like terms, used herein when referring to a dimension or characteristic of a component of the preferred invention, indicate that the described dimension/characteristic is not a strict boundary or parameter and does not exclude minor variations therefrom that are functionally the same or similar, as would be understood by one having ordinary skill in the art. At a minimum, such references that include a numerical parameter would include variations that, using mathematical and industrial principles accepted in the art (e.g., rounding, measurement or other systematic errors, manufacturing tolerances, etc.), would not vary the least significant digit.

Referring to FIGS. 1-15, the preferred invention is directed to a retractor/compression/distraction system, generally designated 10, that permits retraction, distraction and compression of bone segments during a surgical procedure, preferably during a surgical procedure related to a spine segment. The preferred retractor/compression/distraction system 10 is directed to a universal minimally invasive retractor/compression/distraction system 10, but is not so limited and the system 10 may be utilized in open, partially open and other related procedures. The universal minimally invasive retractor/compression/distraction system 10 of the preferred embodiment includes taps 12, blades 14 that are removably mountable to the taps 12 and a base 16 that is removably mountable to the blades 14.

In the preferred embodiment, the taps 12 each include a head 12a and a shaft with threads 12b thereon. The tap 12 is configured to form screw threads in a bone, such as a superior vertebra $V_S$ or an inferior vertebra $V_I$, during the surgical procedure. The tap 12 is not limited to forming threads in the bone and may be configured to form a pilot hole in the bone for introduction of a implant into the pilot hold for use during later portions of the surgical procedure. The tap 12 is also configured for removal from the bone $V_S$, $V_I$ before completion of the surgical procedure, generally meaning that the tap 12 is not an implant that remains in the patient's body following the surgery, but is inserted and removed during the surgical procedure. In the preferred embodiment, the tap 12 includes a first tap 12 and a second tap 12 that are mountable to different bones, such as the superior and inferior vertebrae $V_S$, $V_I$, or may be removably mountable to the same bone during the procedure.

The preferred taps 12 are preferably comprised of cannulated taps 12 that create threads with the tap threads 12b in a bone after a pilot hole is drilled into the bone. The taps 12 preferably create threads in cortical bone that is encountered by the taps 12. The taps 12 may also be self-tapping for forming the threads. The taps 12 preferably include the head 12a that is adaptable and configured to receive a distal end 14c of the blades 14, such that the blades 14 are pivotable relative to the heads 12a of the taps 12 in the mounted configuration and may be locked to the taps 12 for distraction and compression, as will be described in greater detail below. The taps 12 may be placed with an insertion device or tubes (not shown), each of which may assist with the function provided by the taps 12. The taps 12 are not limited to the taps 12 specifically shown in the attached drawings and may be comprised of nearly any provisional non-permanent device that may provide distraction/retraction/compression support, may mark a surgical location for eventual placement of permanent implants, such as a screws, may be threaded or non-threaded, may be cannulated or non-cannulated, may be comprised of a nail/pin/marker, may provide for electrical monitoring of nerves, may attach to the retractor blades 14, may connect to the retractor blades 14 as a single unit or may be connected to the blades 14 before, after or during insertion, may vary in height relative to the bone, i.e above or below the bone or above the skin for different design purposes and may be placed over a guide wire 20 or without a wire. The system 10 may be utilized in spine surgery with our without the guide wire 20, without significantly impacting the design or operation of the system 10 or the procedure. The taps 12 may be used with or without tubes or sleeves for insertion purposes that may assist in the function of the taps 12. The taps 12 may be disposable or re-usable, may be radioluscent or opaque and may connect directly to the base 16 or connect via an intervening device, such as the blades 14, to the base 16. The taps 12 preferably allow for distraction or compression whether directly or via an intervening device.

In the preferred embodiment, the taps 12 may be comprised of any provisionally placed device inserted into the bone, preferably a pedicle of vertebral body, or other boney region in the spine or elsewhere in body to allow attachment to a device for distraction/retraction/compression. The taps 12 are preferably removed following distraction/retraction/compression for possible placement of a final implant such as a screw and, more preferably, a pedicle screw 18. The taps 12 are preferably used during the surgical procedure, but are also, preferably not permanently implanted in the patient post-op. The preferred taps 12 include the threads 12b, but may also be non-threaded. The taps 12 are most preferably threaded to form threads in the bone, as is described herein. The location of the taps 12 preferably become the site of a final implant, such as the pedicle screws 18 that are implanted into the holes with the screw threads created by threads 12b of the taps 12. The taps 12 are not limited to creating the screw threads in the bone and may be relatively smooth, but still form holes for subsequent insertion of a final implant, such as the pedicle screws 18. In the preferred embodiment, the taps 12 are cannulated such that they may be guided to their insertion position by a guide wire 20 and may be able to be placed over a guide wire 20, but are not so limited and the taps 12 may be guided or placed through a tube or sleeve (not shown), implanted with assistance from an inserter (not shown) or generally freehand by a surgeon without a tube or sleeve. The preferred taps 12 are removably connected at their proximal ends to blades 14. The blades 14 are preferably configured for retraction, compression, compaction and distraction. The taps 12 of the preferred embodiment are cannulated and threaded, but are not so limited and may be cannulated and not threaded, non-cannulated and threaded or non-cannulated and non-threaded, depending on the technique being used, the surgery being performed, designer preferences and numerous other factors.

The universal minimally invasive retractor/compression/distraction system 10 of the preferred embodiment does not connect/interdigitate/rely upon connecting to an implanted boney device, such as a screw, hook, pin, nail or other implanted device that remains in the patient following the surgery. The system 10 preferably utilizes a temporarily secured component, such as the taps 12, to engage the bone and provide a relatively stiff and strong component for attachment of retractor blades and/or compression/distraction components to-retract soft tissue, distract bone segments, compress bone segments or otherwise manipulate soft tissue and bone segments, such as a spinal segment, during a surgical procedure.

The blades 14 of the preferred embodiment include a proximal end 14b and a distal end 14c. In use, the distal ends 14b are preferably selectively positionable in the patient near the surgical site and the proximal ends 14a are positioned outside of the patient for grasping and manipulation during the procedure. In the preferred procedure, the distal end is mountable to the head 12a of the tap 12

The system 10 preferably does not include an implanted screw, such as the pedicle screws 18, that are final implants left in the patient at time of closure. The system 10 preferably does include the taps 12, which may be threaded with the threads 12b, non-threaded, solid, cannulated, hooked or any other device that connects to bone, but is preferably not retained within the patient following the surgical procedure.

As described herein, the distraction process relates to separation across bone segments, generally a spinal segment including a superior vertebra $V_S$ and an inferior vertebra $V_I$, whether it be distraction, rotation, flexion, extension or other related movement.

As described herein, the compression process relates to closing or decreasing space across a bone segment, generally a spinal segment including the superior and inferior vertebrae $V_S$, $V_I$, whether it be compression, rotation, flexion, extension or other related movement.

As described herein, retraction relates to an activity that moves tissue out of the way to provide better visualization and access, preferably soft tissue during a surgical procedure. In the preferred embodiment, the blades 14 are confiigures to facilitate soft tissue retraction in the mounted configuration to create a surgical pathway or path to the surgical site. The blades 14 are preferably secured to the heads 12a of the taps 12 in the mounted configuration and the blades 14 retract or urge soft tissue away from and out of the surgical path during use.

As described herein, retractor blades or blades 14 are preferably comprised of devices or instruments that assist in providing at least retraction and, also, preferably, distraction and compression with the preferred system 10.

As described herein, the base or frame 16 is a device that releasably connects to blades 14, independently, together or in various combinations. The base 16 preferably permits manipulation of the blades 14 for retraction of soft tissue, compression of the bone segments and distraction of the bone segments. The base 16 is preferably connected at or near the proximal ends 14b of the blades 14 during use. The base 16 is specifically removably mountable to the proximal ends 14b of adjacent blades 14 during the preferred procedure. The base 16 is configured to manipulate the blades 14 to retract and compress segments of the bone, such as the superior and inferior vertebrae $V_S$, $V_I$, during the preferred surgical procedure. The base 16 preferably includes a gearing system 28 that provides a mechanical advantage to the user when retracting and distracting via the blades 14.

The preferred universal minimally invasive retractor/compression/distraction system 10 is preferably configured for multilevel options that allow staggering of screws 18 and taps 12. The system 10 may be utilized for multilevel procedures, preferably for multilevel spine procedures.

The preferred blades 14 can be rotated to accommodate a second level or further multiple level procedures. In addition, the system 10 may include a lateral or middle level blade (not shown) that can be rotated and move transverse relative to the base 16 to facilitate retraction laterally and/or medially to expand the surgical path.

The system 10 may be utilized for adjacent level, second level surgery by placing the guide wire 20 through cannulated screw 18 and removing screw 18 with subsequent placement of the taps 12 into the holes vacated by the screws 18. The taps 12 may be selected to have a larger diameter in comparison to the screws 18 that are removed from the patient to permit cutting of new screw threads in the bone, preferably along the pedicles of the superior and inferior vertebrae $V_S$, $V_I$. The existing screws 18 may alternatively be preserved in the patient and a connection device may engage the previously inserted screws 18 with screws 18 that are implanted at adjacent or second level surgical sites.

The preferred blades 14 of the system 10 may have multiple lengths to accommodate various patient anatomy, may have the ability to angle out/in (fixed or adjustable) (static angle or dynamic angle), may have the ability to rotate relative to the base 16 or along their length, may be comprised of a disposable material, may provide retractor benefits, may provide distraction/compression benefits, may connect to the taps 12 via eyelets 14a, hooks or fasteners, may connect via post to the inside of cannulated taps 12, may be inserted as one unit with the taps 12, are preferably placed/connected to the taps 12 after the taps 12 are inserted, may be inserted as a combined unit with the taps 12 as a modular or single unit, may be able to rotate around the tap 12 to which it is attached, is preferably connected to the base 16 in a mounted configuration, may act as a fiduciary for image guided systems, are preferably strong enough to sustain forces applied to the blades 14 during normal operation, may be translucent or opaque, may have hinges at single or multiple sites and may connect directly to the base 16 or only to the taps 12 or other independent second base or support structures.

The preferred base 16 of the system 10 connects to the blades 14, preferably at or near the proximal ends 14b, may connect to the taps 12, is preferably configured to allow the blades 14 to angle out statically or dynamically, may be configured to allow the blades 14 to distract a motion segment or bone segments, may allow the taps 12 to angle out statically or dynamically, may connect to other retractor blades 14 in any position within or outside the base 16, may be configured for connection to additional retractor blades 14 that attach to the base 16 independent of the taps 12, may allow the retractor blades 14 and the taps 12 to work independently wherein the retractor blades 14 provide retraction and the taps 12 provide distraction and/or compression, may be connected to a stationary or structural support object (not shown) for additional support or may act as a fiduciary for image guided systems (not shown). The base 16 of the preferred system 10 may include arms (not shown) that extend over the taps 12 and function as retractor blades, may allow the taps 12 and blades 14 to connect independently where each has independent connection and may allow connections to the blades 14 for medial and lateral or other geometric retraction of soft tissue.

In operation, the system 10 is preferably utilized for spinal surgeries, but is not so limited and may be utilized for any procedure related to bones or joints. In a preferred procedure, the system 10 is utilized in a spinal procedure to manipulate a spinal joint, which includes a superior vertebra $V_S$ and an inferior vertebra $V_I$. A preferred spinal procedure utilizing the system 10 may be performed with a spinal needle, such as an 18 gauge spinal needle, a scalpel, a jamshidi needle 22, the guide wire 20, a tissue clearer or spreader, the taps 12, the blades 14, the base 16, a screw driver 24, a tap handle 26 and the screws 18. In an example preferred procedure, the jamshidi needle 22 is used to target a portion of the surgical site associated with the surgical procedure, such as the pedicles of the superior and inferior vertebrae $V_S$, $V_I$, a pilot hole may be drilled into the bone, the guide wires 20 are inserted into the pedicles of the superior and inferior vertebrae $V_S$, $V_I$, the jamshidi needle 22 is removed from the guide wires 20, the tissue clearer/ spreader is moved over the guide wires 20, the depth of the guide wires 20 is measured for tap height and eventual screw length, the depth of the facet-skin surface is measured for retractor blade length, the tissue clearer/spreader is removed from the guide wires 20, the taps 12 are inserted over the guide wires 20 for guiding the taps 12 to the surgical site and driven into the pedicles, the retractor blades 14 are attached to the taps 12, the blades 14 are angled and rotated to provide soft tissue retraction, the base 16 is connected to the blades 14, the superior and inferior vertebrae $V_S$, $V_I$ are distracted and/or compressed across the taps 12 that will ultimately be removed from the patient during the procedure, conduct the procedure, the guide wire 20 is moved through the cannulated taps 12, the base 16 is removed from the blades 14, the taps 12 are removed from the superior and inferior vertebrae $V_S$, $V_I$, the pedicle screws 18 are driven into the pedicles along the screw threads created by the taps 12, nearly any screw 18 can be used from nearly any manufacturer at this point in the procedure for insertion into the pedicle, the guide wires 20 are removed, the rods and caps are added to the screws 18 and the procedure is completed.

Figure 1:
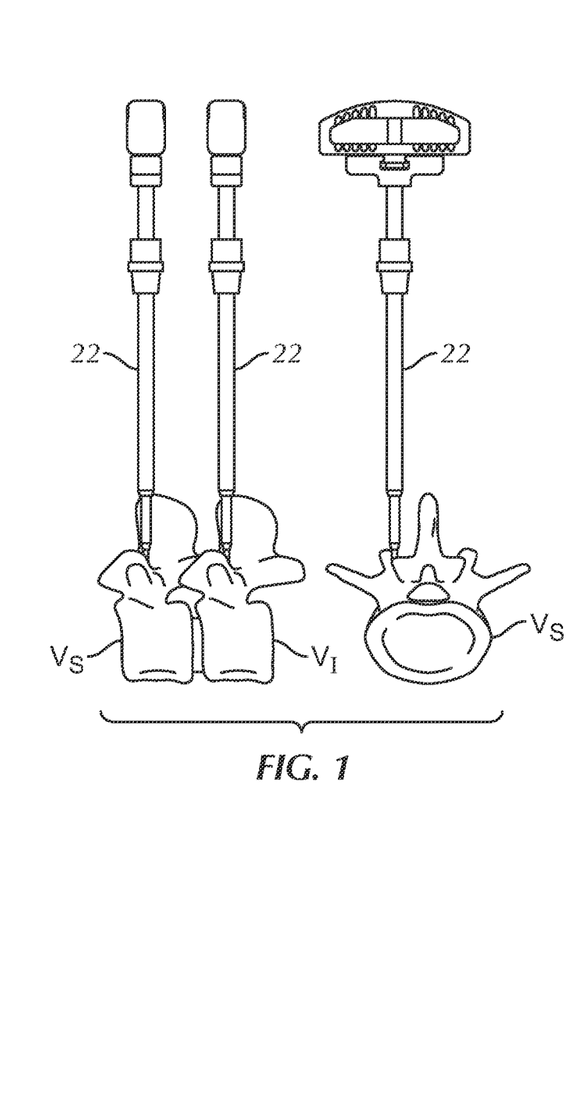
FIG. 1 is right side elevational and top plan views of a prior art jamshidi needle insertion step utilized in the process related to a preferred embodiment of the present invention.
Figure 2:
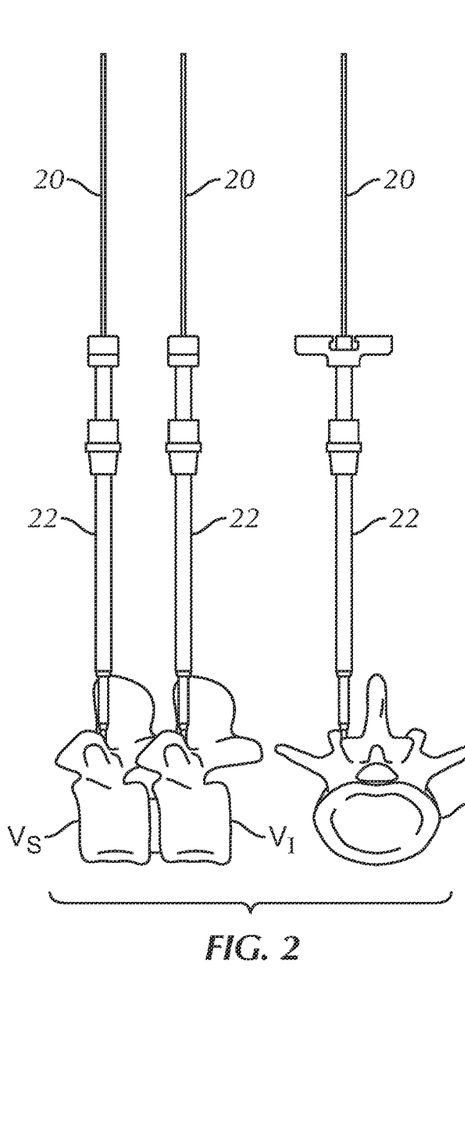
FIG. 2 is right side elevational and top plan views of a prior art guide wire insertion step utilized in the process related to the preferred embodiment of the present invention.
Figure 3:
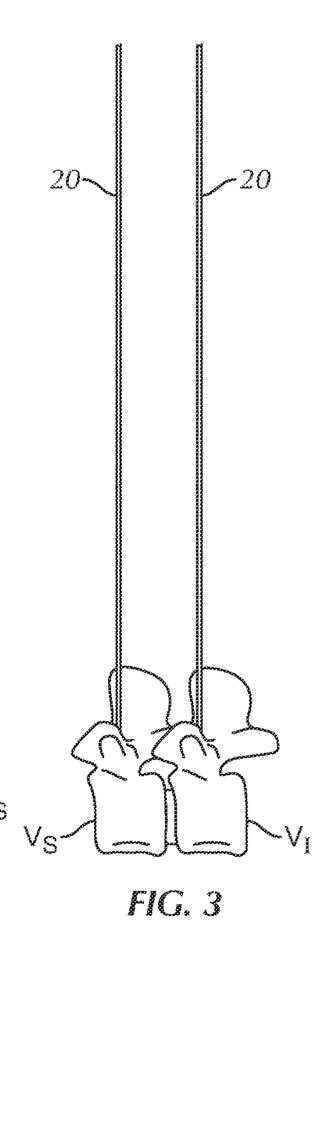
FIG. 3 is a right side elevational view of a prior art jamshidi needle removal in accordance with the process related to the preferred embodiment of the present invention.
Figures 4, 5:
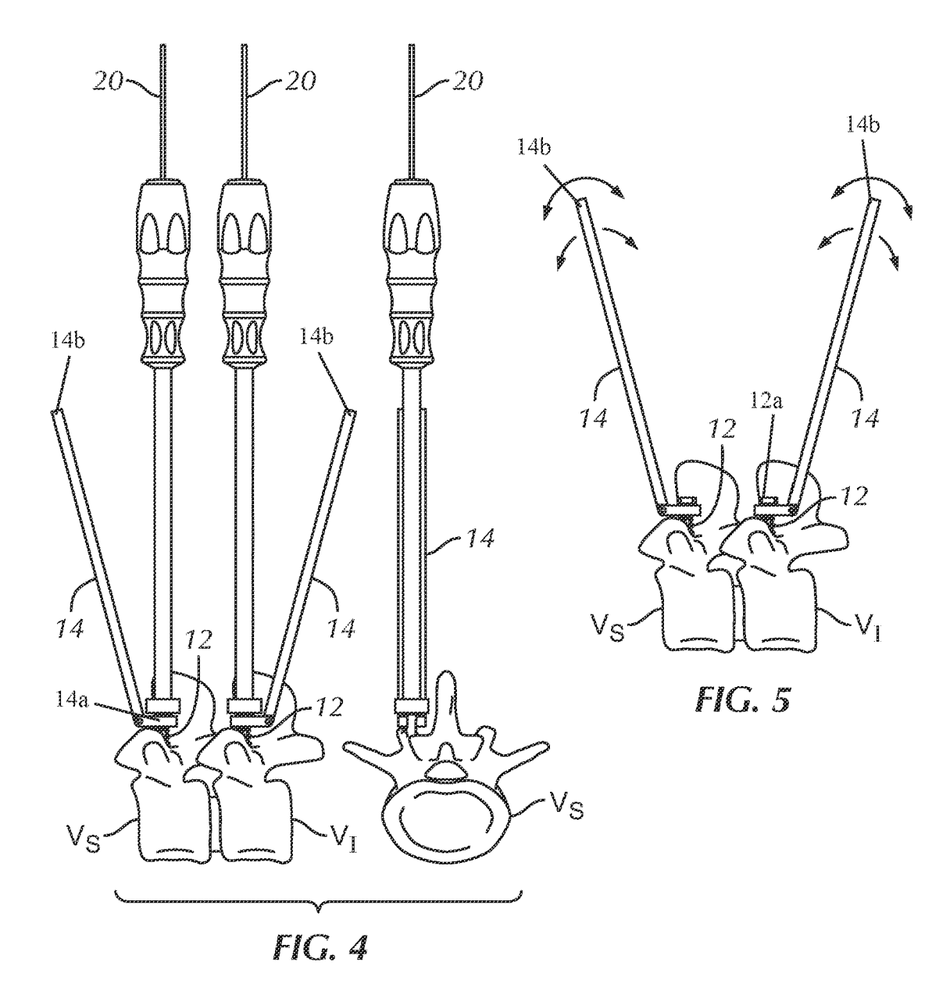
FIG. 4 is right side elevational and top plan views of taps and distractor/retractor blades in accordance with the preferred embodiment of the present invention inserted into a spinal segment.
FIG. 5 is a right side elevational view of the taps and distractor/retractor blades of FIG. 4 with the guide wires removed.
Figure 6:
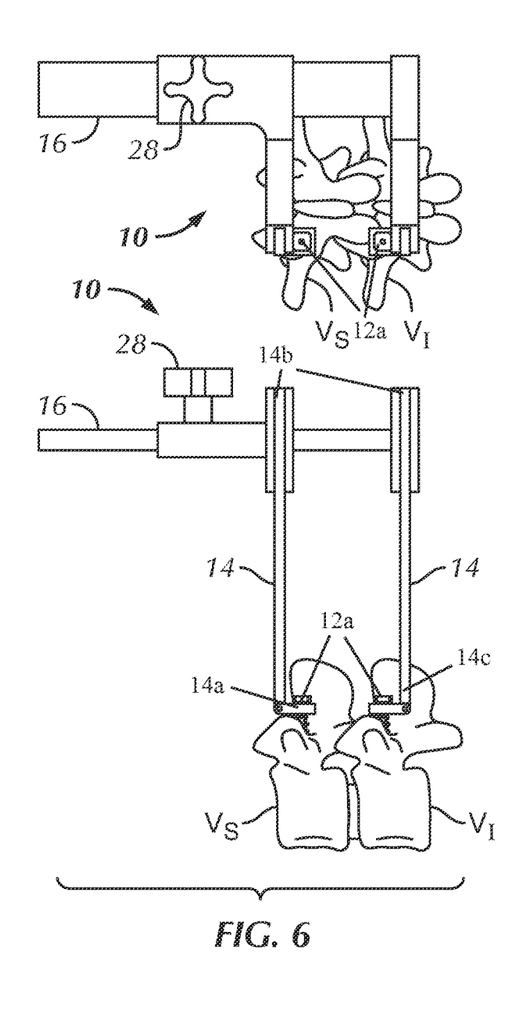
FIG. 6 is right side elevational and rear elevational views of the taps and distractor/retractor blades of FIG. 4 with a retractor/distractor body connected thereto in accordance with the preferred embodiment of the present invention.

In an alternative preferred procedure, the system 10 may be utilized to gain percutaneous access to a pedicle and threading of the pedicle with the taps 12 for decompression of the spine segment including the superior and inferior vertebrae $V_S$, $V_I$, removal of disc material in the spine segment, insertion of a interbody device and placement of the screws 18, rods and caps. In this preferred procedure, the jamshidi needles 22 are placed, the guide wires 20 are inserted through the placed jamshidi needles 22, the jamshidi needles 22 are removed from the pedicles over the guide wires 20 and the taps 12 are placed via the cannulated tap handle 26 over guide wire 20 into the bone. The tap handle 26 is preferably used to urge the tap 12 into the bone. The blades 14 are attached to the taps 12 prior to or following driving the taps 12 into the bone. The blades 14 are preferably attached to the taps 12 such that they are pivotable to assist with retraction of soft tissue (FIGS. 4 and 5). In the preferred embodiment, the blades 14 are removably connected to the taps 12 by an eyelet 14a at the distal end 14c of the blades 14. The eyelet 14a extends over the shaft of the taps 12 and is positioned under a head 12a of the taps 12 in a working configuration to mount the distal end 14c of the blades 14 to the heads 12a of the taps 12, respectively. The blades 14 are not limited to including the eyelets 14a for connection to the taps 12 and may include nearly any connection mechanism that permits connection to the taps 12 and is able to perform the preferred functions of the connection between the blades 14 and taps 12. The eyelets 14a are not limited to be positioned at the distal ends 14c of the blades 14 and may be somewhat spaced from the distal ends 14c, while permitting connection or mounting of the blades 14 to the heads 12a, respectively. The connection options may allow independent placement of the blade 14 to attach to the taps 12 after the taps 12 are inserted into the bones. The taps 12 and blades 14 may also be inserted to the surgical site through tubes (not shown) to assist placement. The blades 14 may be attached to taps 12 while the taps 12 are inserted into the pedicles of the superior and inferior superior and inferior vertebrae $V_S$, $V_I$. Following insertion of the taps 12 and potentially the blades 14, the guide wires 20 and/or any additional insertion instruments are removed from the surgical path. Following removal of the guide wires 20, the preferred blades 14, with their hinged and pivoting ability, are able to aid with retraction of soft tissue while attached to the taps 12 to increase visualization of the surgical site.

Following removal of the guide wires 20, the base 16 is preferably attached directly to blades 14 at or near the proximal ends 14b of the blades 14. The blades 14 may also be hinged at various angles relative to the base 16 to customize the surgical path and retraction of soft tissue, but are preferably in a substantially perpendicular orientation relative to the blades 14, as is shown in FIGS. 6-9. In this preferred example procedure, once the blades 14 are attached to the base 16, the blades 14 can be distracted away from each other to provide distraction of the spinal segment, thereby moving the superior vertebra $V_S$ away from the inferior vertebra $V_I$. The distraction occurs as the blades move apart as they are attached to the taps 12 causing the bones to move away from each other. Similarly, if and when desired, compression can be applied by urging the blades 14 and taps 12 toward each other using the base 16, which preferably includes a mechanical advantage mechanism 28, such as a gearing system 28 to move the blades 14 relative to each other. In this preferred embodiment the mechanical advantage mechanism 28 of the base 16 is comprised of a ratcheted system 28 with articulating/hinged parts that allow bending of the system 10 out of the way of the surgical field and the surgical path.

Figure 7:
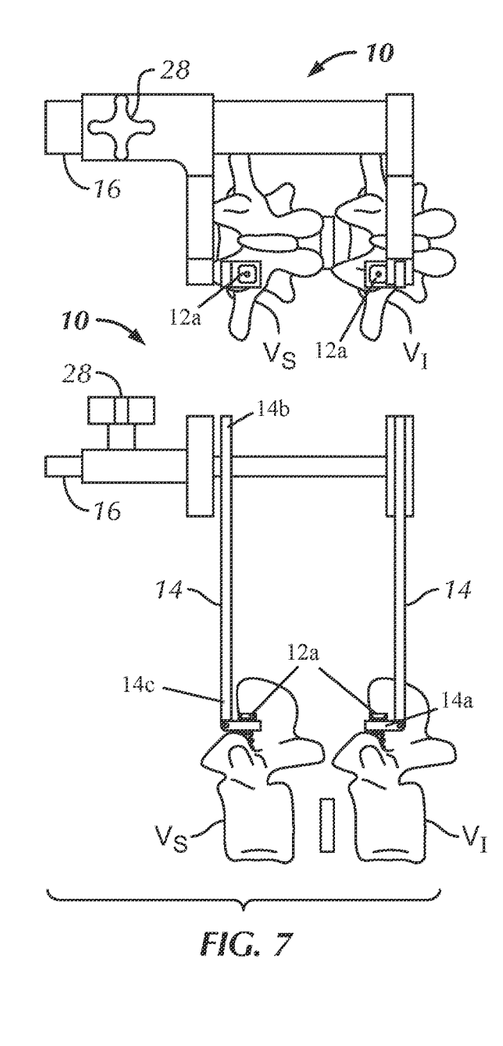
FIG. 7 is right side elevational and rear elevational views of the assembly of FIG. 6, wherein the spinal segment is distracted.

Referring to FIG. 7, the base 16, blades 14 and taps 14 are utilized to distract the interbody disc space or motion segment. The disc in the segment is shown as floating freely in the lower schematic in this segment for illustration purposes only, as the disc would typically remain attached to the superior and inferior vertebrae $V_S$, $V_I$ during distraction, often from an overly compressed configuration prior to the surgical procedure.

The preferred system 10 is configured for potential distraction, retraction and/or compression across segmental motion segments or between segments of bone. The taps 14 are preferably mounted to the bone for distraction, retraction and/or compression of the motion segment or the bone segments, removal from the bone and for potential placement of permanent devices during the procedure.

Figure 8:
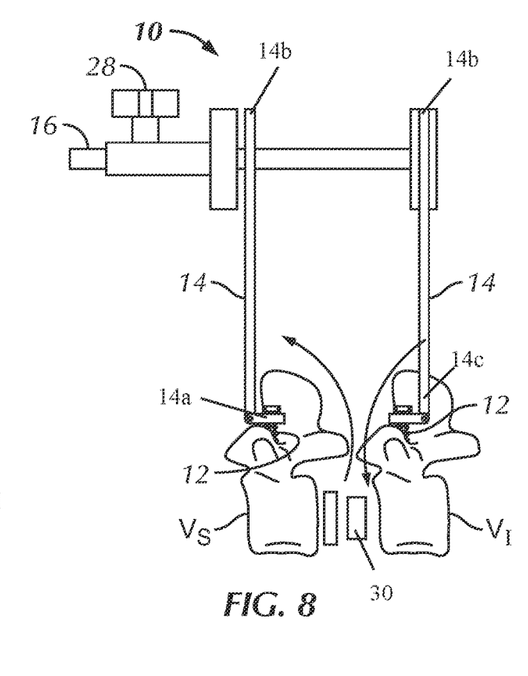
FIG. 8 is a right side elevational view of the assembly of FIG. 6, wherein disc material is being removed and an interbody device is inserted in the disc space.

Referring to FIG. 8, the disc material is then preferably removed or extracted and an interbody implant 30 is chosen and placed between the superior and inferior vertebrae $V_S$, $V_I$ by the surgeon. Portions of the superior and inferior vertebrae $V_S$, $V_I$ may also be removed to clear additional space from the spinal segment to create some blood flow and increase the usable space. Placement of the interbody implant 30 is not limiting and the surgeon may conduct alternate procedures not involving the interbody implant 30. The surgeon may perform other surgical procedures at this step including bone resection, such as a laminectomy, a laminotomy or other related procedures.

Figure 9:
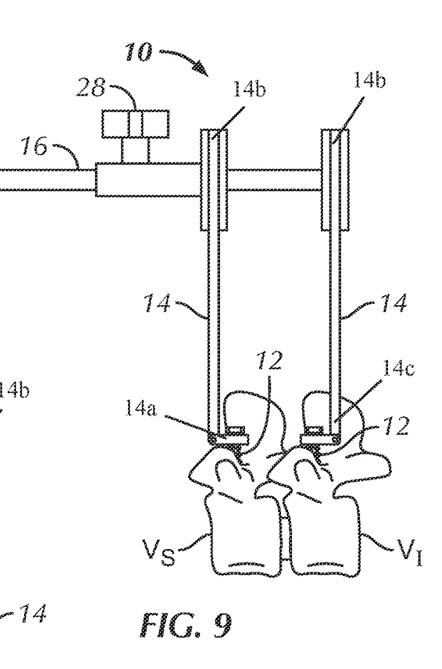
FIG. 9 is a right side elevational view of the assembly of FIG. 6, wherein the spinal segment is compressed.

Referring to FIG. 9, the system 10 may also be utilized to provide compression at this stage of the procedure, if desired. The gearing or ratcheting system 28 drives the blades 14 and taps 12 toward each other to create compression between the superior and inferior vertebrae $V_S$, $V_I$, and the interbody spacer 30. Alternatively, the taps 12 and blades 14 may be comprised of a single unit and have features that permit rotation, pivoting, flexing and extending to facilitate retraction of soft tissue. Further, insertion devices (not shown) for the taps 12 or blades 14 may be utilized to retract/distract/compress. The insertion devices may be placed through tubes that may also assist with retraction, distraction and/or compression.

Figure 10:
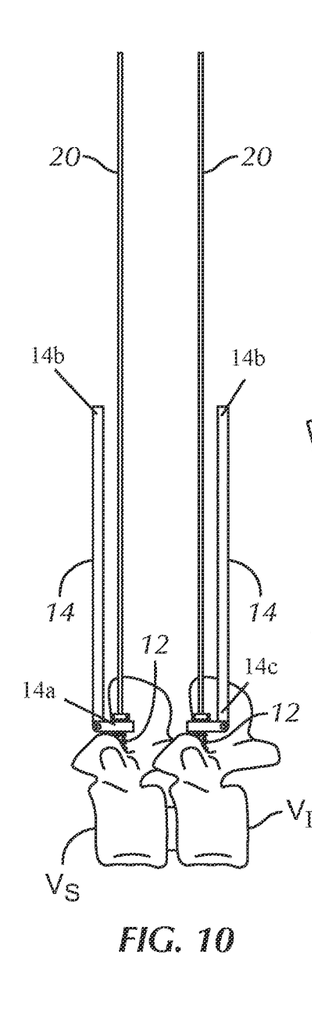
FIG. 10 is a right side elevational view of the taps and distractor/retractor blades of FIG. 4, wherein the retractor/distractor body is removed and guide wires are inserted.

Referring to FIG. 10, the base 16 is removed from the blades 14 and the guide wires 20 are re-inserted directly into the cannulations in the taps 12. In this preferred embodiment, tubes are not used to place the guide wires 20 as they are placed with direct visualization. In this preferred embodiment the base 16 is removed after the guide wires 20 are placed, but the procedure is not so limited. The procedure may alternatively be performed using inserters with the guide wires 20 being placed through the insertion devices. In a further alternative procedure, the taps 12 may be solid without cannulation, such that guide wires 20 are not required for the procedure.

Figure 11:
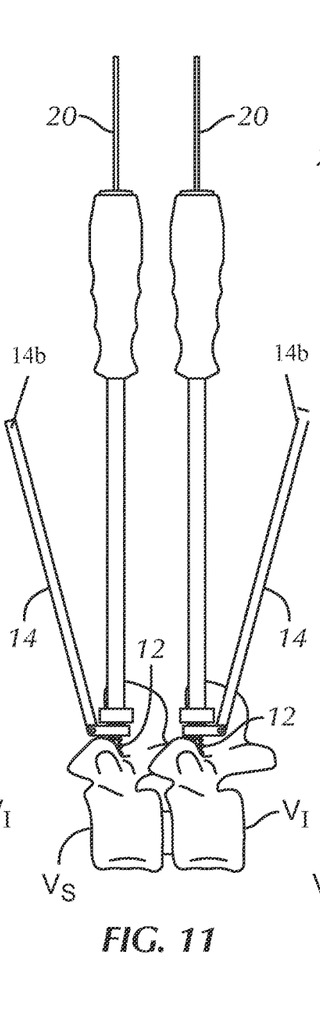
FIG. 11 is a right side elevational view of the taps and distractor/retractor blades of FIG. 4, wherein tap handles are inserted to remove the taps and distractor/retractor blades.

Referring to FIG. 11, the tap handle 26 is moved over the guide wire 20 to reattach to the taps 12. The cannulated tap handle 26 preferably does not attach to the blades 14. In other preferred embodiments, guide tubes may be used to guide the tap handle 26. In other embodiments, the blades 14 may be used to place tubes and help guide the guide wire 20 back into the taps 12.

Figures 12, 13:
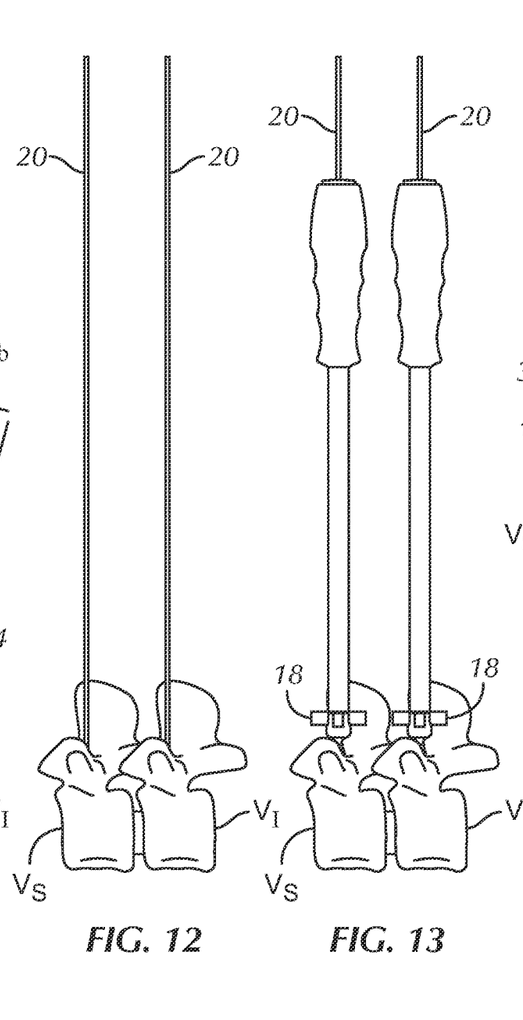
FIG. 12 is a right side elevational view of the spinal segment with the guide wires inserted therein and the taps and distractor/retractor blades of FIG. 4 removed.
FIG. 13 is a right side elevational view of cannulated screws inserted into the vertebrae of the spinal segment.

Referring to FIG. 12, the taps 12, blades 14 and tap handle 26 are removed from the surgical site. The guide wires 20 are preferably retained in the pre-formed holes with screw threads in the bones. At this point, surgical options may include placement of pedicle screws 18 of surgeon's choice, including solid, cannulated, hooks, rods or other implants. The screws 18 or other implants may even be selected at this stage of the procedure to optimize the advantages of various systems. Alternatively, the surgeon may or may not choose to place any permanent implants into or near the bones at this stage of the procedure.

Referring to FIG. 13, the guide wires 20 that are left behind from are preferably being used for placement of cannulated permanent screws 18 with use of the cannulated screw driver 24. These screws 18 can be from any number of existing spine systems, as the preferred system 10 is not limited to being used with any particular screw system. In addition, the insertion of permanent implants is not required and a surgeon may perform a procedure with the preferred system 10 without inserting permanent implants.

Figure 14:
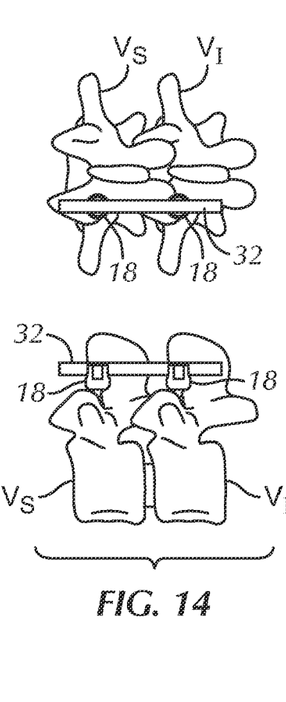
FIG. 14 is a right side elevational and rear elevational views of a rod secured to the cannulated screws that are secured to the spinal segment.
Figure 15:
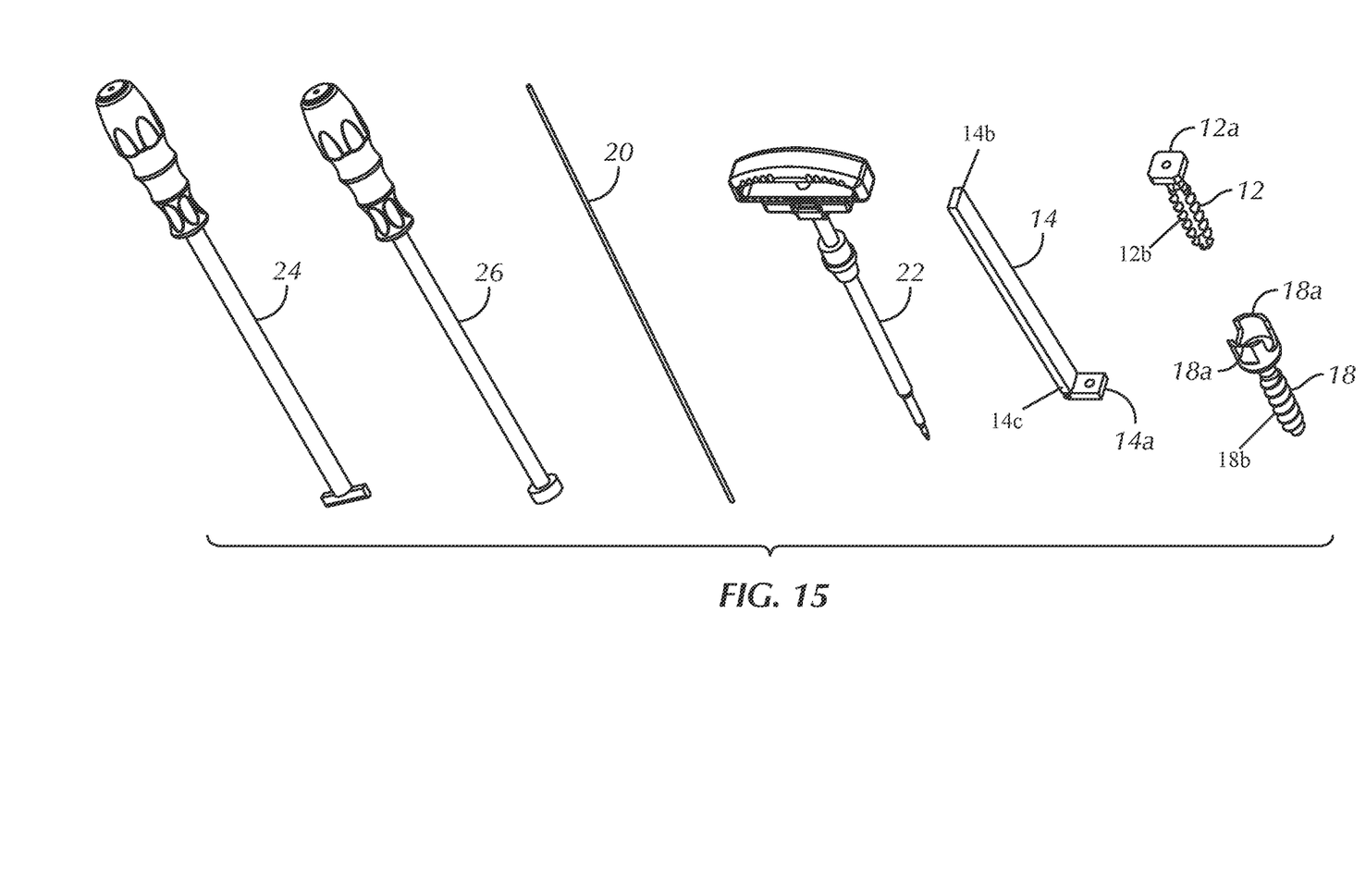
FIG. 15 is a series of side perspective views of various instruments, implants and components utilized in the procedure related to the preferred process of the present invention.

Referring to FIG. 14, the screw 18 preferably includes a threaded distal portion 18b and a tulip head 18a at a proximal portion. The screw 18 is configured to engage the screw threads formed in the bone by the taps 12 after the tap 12 is removed from the bone. For example, the taps 12 may form threads in the pedicle area of the superior or inferior vertebra $V_S$, $V_I$, and the threaded distal portion 18b is configured to engage the threads in the pedicle portion after the tap 12 is removed from the bone. The tulip head 18a is preferably configured to accept placement of rods 32, which can be accomplished in multiple fashions using screw and rod systems.

Referring to FIGS. 1-15, the preferred system 10 may be utilized for various procedures and in various areas of the body, including in the lumbar spine, in the sacrum, in the pelvis, in the thoracic spine, in the cervical spine, with the skull, for spanning and connecting as is shown in FIGS. 1-6, in other boney non-spine procedures, in repeat spine surgeries involving same level repeat surgery, adjacent levels to be connected to previous surgery, as well as non-contiguous levels, with additional retractor blade optional attachments to the base 16 to provide medial and lateral benefits and in other related procedures and processes.

In the application of spine surgery, the preferred system 10 provides a universal system that allows better visualization of a surgical field than if permanent bulky screws were placed as the anchoring point for a retractor system. Alternatively, FSS are also available requiring anchoring to other fixed devices. In the application of spine surgery this device may provide a distinctly different technique with regards to the order of surgical events for spine surgery that does not require engaging the distraction or compression systems to permanent implants, to the surgical table, or to other separate structures that are not otherwise utilized during the surgical procedure.

The preferred retractor/compression/distraction system 10 attaches to provisionally placed pins/screws/taps 12 ("taps"), which may include the threads 12*b*, but may also be non-threaded or otherwise modified to mount to the bone segment. The taps 12 of the preferred embodiment may be exchanged for eventual permanent screw/pin/instrument placement, such as the pedicle screws 18. The taps 12 of the preferred embodiment may be cannulated/slotted, or solid or with modifications that may allow ease of exchange for other devices or removal. The preferred taps 12 may serve to aide in retraction and exposure or allow attachment to other devices, such as the preferred blades 14, that may add to retraction or exposure. The taps 12 may assist in distraction/compression/rotation of the bones/tissue for which they are implanted or impact other areas. In addition, other devices may be attached to the taps 12 that assist in distraction/compression/rotation of the bones/tissues in the surgery either directly or indirectly. The preferred retractor/exposure system 10 may be used for future placement of instrumentation or just used for decompression, exposure and non-permanent implant purposes. The preferred retractor system 10 may be utilized any type of spine or bone surgery including cervical, thoracic, lumbar, sacral, pelvic or procedures extending across multiple segments. The preferred system 10 may also be utilized from all anatomic exposure angles included and not limited to anterior, posterior, lateral or any angle in between.

The base 16 of the preferred embodiment may be directly connected to the taps 12 via a number of possibilities or via an intermediary such as the blade 14 that attaches from the tap 12 to the base 16. The base 16 may fixed solely to the taps 12 or in combination to an outside stabilizing attachment, such as to a table or other mountable object.

The system 10 may be utilized to determine instrumentation sizes and contour for screws 18 and rods 32 or other implants that are utilized during the surgical procedure, such as the interbody implant 30. The taps 12 of the preferred embodiment may be utilized to determine definitive instrumentation sizes and contour for the screws 18 and rods 32 and other implants, including the preferred interbody implant 30. Measuring the distance between the taps 12 in the implanted configuration will help determine characteristics of additional instrumentation to be utilized. In addition, the preferably provisional taps 12 will be able to be used with imaging technology to include but not limited to intraoperative three-dimensional ("3D") imaging to assist in determining characteristics of final proposed instrumentation/implants and potentially help with improving/maintaining alignment and balancing concerns.

It will be appreciated by those skilled in the art that changes could be made to the embodiment described above without departing from the broad inventive concept thereof. It is understood, therefore, that this invention is not limited to the particular embodiment disclosed, but it is intended to cover modifications within the spirit and scope of the present invention as defined by the present disclosure.

What is claimed is:

1. A kit comprising:
   a first blade having a first proximal end and a first distal end, wherein: (a) the first distal end is mountable to a first head of a first rod, (b) the first blade is pivotable relative to the first head in a first mounted configuration, and (c) the first blade is configured to facilitate soft tissue retraction in the first mounted configuration to create a surgical path to a surgical site;
   a second blade having a second proximal end and a second distal end, wherein: (a) the second distal end is mountable to a second head of a second rod, (b) the second blade is pivotable relative to the second head in a second mounted configuration, and (c) the second blade is configured to facilitate soft tissue retraction in the second mounted configuration to create the surgical path to the surgical site;
   a base removably mountable to the first and second proximal ends, the base being configured to manipulate the first and second blades to manipulate at least one of the first or second rods during a surgical procedure;
   wherein the first rod has a first shaft with first threads and the first head and the second rod having a second shaft with second threads and the second head;
   wherein (a) the first blade includes a proximal third, a middle third, and a distal third, (b) the middle third is between the proximal and distal thirds, (c) the proximal and distal thirds extend to opposing ends of the first blade, (d) the distal third includes a hinge and an aperture, and (e) the hinge is between the aperture and the middle third;
   wherein (a) a portion of the distal third of the first blade includes an axis that extends through the middle and proximal thirds, (b) the hinge includes a hinge axis about which the hinge rotates, and (c) the portion of the distal third of the first blade is configured to pivot about the hinge axis such that the axis has a plurality of orientations with respect to the hinge axis and in at least one of the plurality of orientations the axis is not parallel to the hinge axis.

2. The kit of claim 1, wherein in the at least one of the plurality of orientations the axis is orthogonal to the hinge axis.

3. The kit of claim 2, wherein the axis interests the hinge axis.

4. The kit of claim 3, wherein the axis does not intersect the aperture.

5. The kit of claim 4, wherein the hinge axis does not intersect the aperture.

6. The kit of claim 5, wherein:
   the first blade includes a monolithic surface;
   the monolithic surface defines a continuous unbroken perimeter;
   the continuous unbroken perimeter defines an entry to the aperture.

7. The kit of claim 5, wherein the aperture completely passes through the first blade forming a tunnel with more than one entry to the tunnel.

8. The kit of claim 7, wherein in the first mounted configuration the aperture is configured to extend distal to the first head such that at least a portion of the first head is between the aperture and the base.

9. The kit of claim 8, wherein the first blade is configured to lock to the first rod.

10. The kit of claim 8, wherein the first rod includes a first tap and the second rod includes a second tap.

11. The kit of claim 7, wherein the aperture is configured to receive the first rod.

12. The kit of claim 11, wherein the base includes a gear.

13. The kit of claim 11 comprising a third blade coupled to the base, wherein:
   the first blade is configured to slide along the base in a first direction;

the third blade is configured to slide in a second direction that is orthogonal to the first direction.

14. The kit of claim 11, wherein the kit does not include either of the first or second rods.

15. The kit of claim 11, wherein the first and second rods are cannulated.

\* \* \* \* \*